United States Patent [19]

Beattie et al.

[11] Patent Number: 4,474,806
[45] Date of Patent: Oct. 2, 1984

[54] SULFONYL OR CARBONYL INOSITOL DERIVATIVES USEFUL AS ANTI-INFLAMMATORY/ANALGESIC AGENTS

[75] Inventors: Thomas R. Beattie, Scotch Plains; Shu S. Yang, Bridgewater, both of N.J.

[73] Assignee: Merck & Co., Inc., Rahway, N.J.

[21] Appl. No.: 376,364

[22] Filed: May 10, 1982

[51] Int. Cl.³ .............. C07C 125/065; C07C 127/15; A61K 31/325; A61K 31/17

[52] U.S. Cl. .................................. 424/300; 424/301; 424/303; 424/304; 424/305; 424/308; 424/309; 424/310; 424/311; 424/312; 424/313; 424/314; 424/320; 424/321; 424/322; 424/324; 260/404; 260/408; 260/410; 260/413; 260/455 B; 260/456 R; 260/456 A; 260/456 P; 260/457; 260/464; 260/465 D; 260/928; 260/938; 260/944; 260/456 F; 560/9; 560/18; 560/20; 560/22; 560/28; 560/29; 560/31; 560/32; 560/41; 560/47; 560/49; 560/50; 560/55; 560/56; 560/64; 560/65; 560/72; 560/75; 560/100; 560/104; 560/105; 560/106; 560/115; 560/125; 560/126; 560/128; 560/148; 560/159; 560/160; 560/161; 560/162; 560/173; 560/183; 560/188; 560/193; 560/219; 560/220; 560/194; 564/48; 564/49; 564/50; 564/52; 564/53; 564/56; 564/57; 564/79; 564/80; 564/82; 564/83; 564/86; 564/87; 564/89; 564/93; 564/96; 564/98; 564/155; 564/161; 564/166; 564/168; 564/174; 564/183; 564/191; 564/193; 564/201; 564/204; 564/210; 564/217; 564/228; 564/231; 564/107; 549/360; 549/358

[58] Field of Search ............... 560/162, 115, 9, 12, 560/22, 28, 31, 32, 148, 159, 160, 161; 260/465.4, 465 D; 424/300, 322; 564/49, 48, 50, 52, 53, 56, 57, 58, 59, 60

[56] References Cited

U.S. PATENT DOCUMENTS

| | | |
|---|---|---|
| 2,997,490 | 5/1959 | Huber . |
| 2,997,491 | 9/1959 | Huber . |
| 3,207,780 | 9/1965 | Argoudelis ............... 560/162 |
| 3,470,295 | 9/1969 | Revici ..................... 424/343 |
| 4,033,971 | 7/1977 | Hauck ..................... 560/162 |

OTHER PUBLICATIONS

Wilson, "Textbook of Organic Medical and Pharmaceutical Chemistry," pp. 39-40, (1954).
Roche, "Design of Biopharmaceutical Properties Through Prodrugs and Analogs," pp. 281-285, 299-304 & 311-315, (1977).
Dewert Abst. of Jap. Pat. 48-49743.

*Primary Examiner*—Michael L. Shippen
*Attorney, Agent, or Firm*—Theresa Y. Cheng

[57] ABSTRACT

Sulfonyl or carbonyl derivatives of inositols are found to be effective phospholipase C inhibitors and thereby potent anti-inflammatory and analgesic agents. These inositol derivatives are prepared by condensation of a protected inositol with a substituted sulfonic or carboxylic acid derivative followed by removal of protecting groups.

7 Claims, No Drawings

SULFONYL OR CARBONYL INOSITOL DERIVATIVES USEFUL AS ANTI-INFLAMMATORY/ANALGESIC AGENTS

BACKGROUND OF THE INVENTION

A group of novel sulfonyl or carbonyl inositol (PI) derivatives are found to be effective phospholipase C inhibitors which are useful anti-inflammatory and analgesic agents.

Phospholipase C contained in mouse peritoneal macrophages has been linked to the enhanced turnover of phosphatidyl inositols which in turn has been suggested by recent studies as one of the sources of arachidonic acid. It has been established that a rapid synthesis of prostaglandins (PG) from arachidonic acid in macrophages usually accompanies inflammatory stimuli. Thus, inhibition of the release of arachidonic acid from macrophages would provide an effective control of PG synthesis and thereby inflammatory conditions. Recently, phospholiphase C has been characterized as an enzyme which is involved in the biosynthetic phosphatidylinositol-arachidonic acid-prostaglandin pathway. This finding is further substantiated by the observation that phospholipase C is inhibited by phenothiazine, a compound known to inhibit the stimulated release of arachidonic acid from macrophages and prostaglandins from platelets.

Accordingly, it is an object of this invention to provide specific and selective inhibitors of phospholipase C which can be potent anti-inflammatory and analgesic agents useful in the treatment of inflammatory conditions, including rheumatoid arthritis, emphysema, bronchial inflammation, osteoarthritis, spondylitis, lupus, psoriasis, acute respiratory distress syndrome, gout, fever, and pain.

Another object of this invention is to provide pharmaceutical compositions to be used in the administration of the novel phospholipase C inhibitors, which are novel sulfonyl or carbonyl inositol derivatives.

Still a further object of this invention is to provide a method of controlling and treating inflammation and pain by administering an effective amount of the novel inositol derivatives in a mammalian species in need of such treatment.

Finally, it is also an object of this invention to provide a process for preparing the novel inositol derivatives.

DETAILED DESCRIPTION OF THE INVENTION

This invention relates to novel phosphatidyl inositol analogs of the structural formula I and II.

$$L-\overset{O}{\underset{O}{\overset{\|}{S}}}-Y-A \quad\quad L-\overset{O}{\overset{\|}{C}}-Y-A$$

$$(I) \quad\quad\quad (II)$$

or a pharmaceutically acceptable acid, ester, ether or carbonate thereof.

wherein:

L is
  (a) hydrogen;
  (b) $R^1$; where $R^1$ is
    (1) straight or branched-chain alkyl having from 1 to 20 carbon atoms, such as methyl, ethyl, isopropyl, t-butyl, n-hexyl, n-heptyl, n-decyl, isododecyl, n-pentadecyl, n-hexadecyl, n-octadecyl, and n-eicosyl;
    (2) aryl having from 6 to 10 carbon atoms especially phenyl, substituted phenyl or naphthyl with the proviso that L cannot be p-tolyl when A is myo-inositol;
    (3) cycloalkyl having from 3 to 8 carbon atoms, especially cyclopentyl or cyclohexyl;
    (4) alkenyl having from 2 to 20 carbon atoms especially $C_{8-20}$ alkenyl such as n-octenyl, i-decenyl, i-dodecenyl, n-tetradecenyl, n-octadecenyl, nonadecenyl or arachidonyl;
    (5) cycloalkenyl having from 5 to 8 carbon atoms, especially cyclopentenyl or cyclohexenyl;
    (6) aralkyl, alkaryl, aralkenyl, alkenylaryl, wherein alkyl, aryl, and alkenyl are as previously defined;

The above groups (1) to (6) are unsubstituted or substituted by radicals, for example, hydroxy; alkoxy; halo such as fluoro, chloro, bromo or iodo; cyano; carboxy; amino; substituted amino such as mono $C_{1-6}$ alkylamino and di($C_{1-6}$ alkyl) amino; carbamoyl; sulfonyl; sulfinyl; thio(SH); alkylthio, nitro or the like. Representative examples of these substituted groups are hydroxyethyl, 3-methoxypropyl, 4-hydroxyphenyl, 3- or 4-chlorobenzyl, 4-trifluoromethylbenzyl, 2-aminophenethyl, 2-carboxyphenylethenyl, 4-cyanomethylphenyl, 2,6-dimethoxyphenyl, 2-ethoxy-1-naphthyl, 4-amino-4-carboxybutyl, 1-naphthylmethyl, 1-(N-ethylaminophenyl)-n-butyl, 2-carbamoylbenzyl, 2-methylthiophenyl, 2,4-dinitrobenzyl, −CH$_2$−⟨biphenyl⟩, and −CH$_2$CH$_2$−⟨phenyl⟩−O−⟨phenyl⟩;

(c)

$$\underset{CH_2-CH-(CH_2)_n-}{\overset{OR^2 \quad OR^3}{| \quad\quad |}}$$

where $R^2$ and $R^3$ independently are:

loweralkyl especially $C_{1-20}$ alkyl such as methyl, ethyl, isopropyl, t-butyl, n-pentyl or isoheptyl; (1)

$$-\overset{O}{\overset{\|}{C}}-loweralkyl \quad (2)$$

$$-\overset{O}{\overset{\|}{C}}-CH_2-⟨biphenyl⟩; \quad (3)$$

$$-\overset{O}{\overset{\|}{C}}-CH_2CH_2-⟨phenyl⟩-O-⟨phenyl⟩; \quad (4)$$

-continued

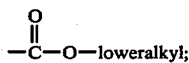 (5)

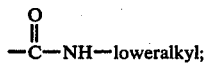 (6)

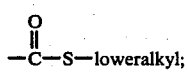 (7)

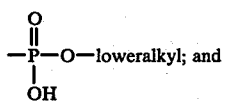 (8)

n is an integer from 0 to 4;

(d)

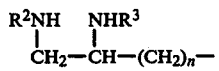

wherein $R^2$, $R^3$, and n are as defined previously; or
(e) $R^1NH-$;
(f) HO— or $R^1O$ wit the proviso that L is adjacent to a carbonyl group as represented by formula (II); or
(g)

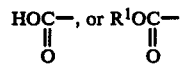

providing that L is adjacent to a carbonyl group as represented by formula II;
Y is oxygen, —NH— or methylene; and
A is a radical of
(a) myo-inositol or a configurational isomer thereof, such as scyllo-inositol and chiro-inositol, for example,

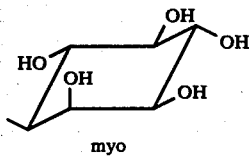

myo (b) branched chain myo-inositol, for example,

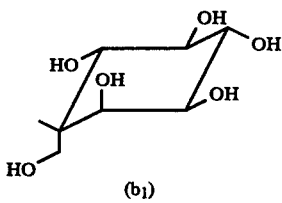 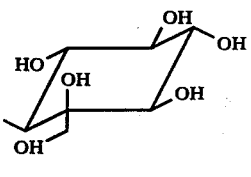

(b₁)  (b₂)

(c) 2-,4 or 5-positional isomer of myo-inositol, for example

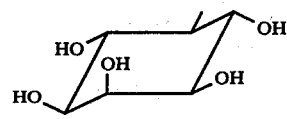

(c₁) 5-isomer;

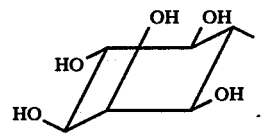

(c₂) 4-isomer;

(d) inositol substituted with a radical such as amino; azido; deoxy; halo especially fluoro or chloro; and loweralkyl especially $C_{1-6}$ alkyl such as methyl, ethyl, isopropyl, t-butyl, amyl or n-hexyl;
(e) branched-chain inositol of the structural formula

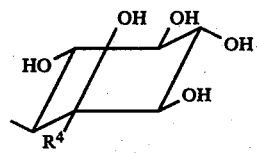 (e)

where $R^4$ is $C_{1-6}$ alkyl or substituted $C_{1-6}$ alkyl especially halomethyl such as fluoromethyl, trifluoromethyl, methyl, 2-methoxyethyl, ethyl, isopropyl, t-butyl, pentyl or -methoxyhexyl
(f) substituted inositols having one or more of its hydroxy groups coupled with another

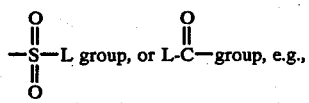

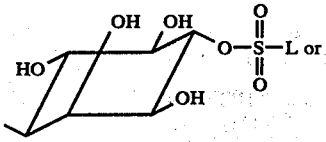

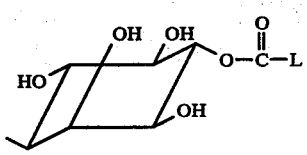

and

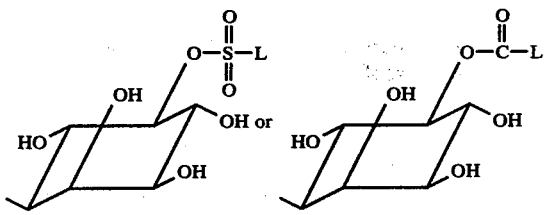

(g) epimeric inositols which are linked to Y at positions configurationally opposite to those found in myo-inositol such as

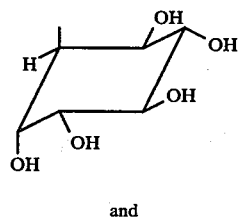

and

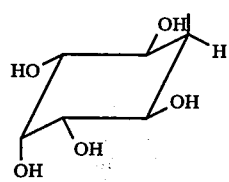

The preferred embodiment of this invention relates to a compound of Formula (I) or (II) wherein:

L is
(a) $R^1$;
(b) $R^1NH$;
(c)

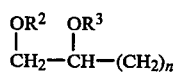

where $R^2$ and $R^3$ are as previously defined;
(d) HO— or $R^1O$ when L is adjacent to a carbonyl group; or
(e)

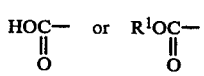

when L is adjacent to a carbonyl group;
Y is oxygen, —NH— or methylene; and
A is a radical of
(a) myo-inositol;
(b) branched-chain myo-inositol;
(c) branched-chain inositol of formula (e);
(d) epimeric myo-inositol; or
(e) substituted inositol having one or more of its hydroxy groups coupled with another

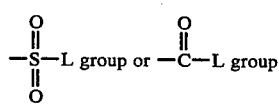

The most preferred embodiment of this invention relates to a compound of formula (I) wherein L is (a) $R^1$ where $R^1$ is $C_{1-20}$ alkyl,

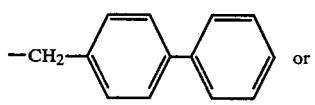

-continued

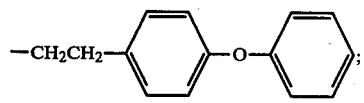

(b) $\underset{|}{OR^2}\ \underset{|}{OR^3}$
$CH_2-CH-(CH_2)_n$— where $R^2$ and $R^3$ independently are:

(1) $C_{1-20}$ alkyl;

(2) $-\underset{\underset{O}{\|}}{C}-R^1$ where $R^1$ is $C_{7-20}$ alkyl,

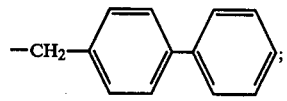

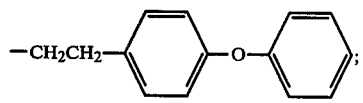

$-\underset{\underset{O}{\|}}{C}-OC_{7-20}$ alkyl;

$-\underset{\underset{O}{\|}}{C}-NHC_{7-20}$ alkyl; or (3) hydrogen;
n is 1-2;

(c) HO, $R^1O$, $R^1O-\underset{\underset{O}{\|}}{C}-$ or HO$-\underset{\underset{O}{\|}}{C}-$ when L is adjacent to a carbonyl group and wherein $R^1$ is (1) $C_{1-20}$ alkyl;

(2) 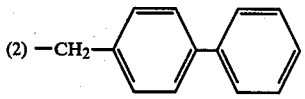

(3) 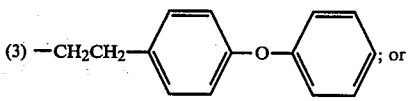

(d) $R^1NH-$ where $R^1$ is $C_{1-20}$ alkyl;

Y is oxygen or nitrogen; and
A is a radical of myo-inositol with at least one substituent at any of the ring positions.

The novel compounds of the present invention wherein Y is O are generally prepared by a process comprising the treatment of a protected inositol derivative of formula HOAT with a sulfonyl or carboxylic acid halide of formula III or anhydride of formula IIIa followed by removal of the protecting groups:

STEP (1)

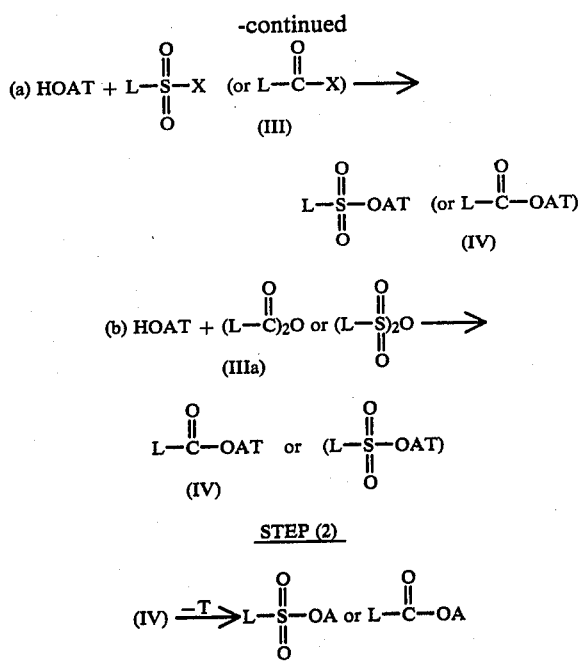

STEP (2)

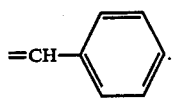

wherein A is an inositol radical as previously defined; X is halo such as chloro or bromo and T is a protecting group for —OH, especially unsubstituted or substituted benzyl such as benzyl, p-methoxybenzyl, m or p-nitrobenzyl, p-carboxymethylbenzyl, m-fluorobenzyl, o,p-dichlorobenzyl and p-methylthiobenzyl; and substituted or unsubstituted alkylidene especially $C_{1-5}$ alkylidene, for example, ethylidene, isopropylidene, cyclopentylidene, cyclohexylidene, or =CH-aryl such as

=CH—⌬.

Other processes are further illustrated in Examples 2-6, pages 21-27.

Most of the starting materials of the processes described above are commercially available or known in the literature. A few new fluoro derivatives of inositols, for example, D L-1-O-benzoyl-2-C-fluoromethyl-3,4,5,6-tetra-O-benzyl-myo-inositol and 1-O-benzoyl-2-fluoro-2-deoxy-3,4,5,6-tetra-O-benzyl-scyllo-inositol are prepared according to the following scheme:

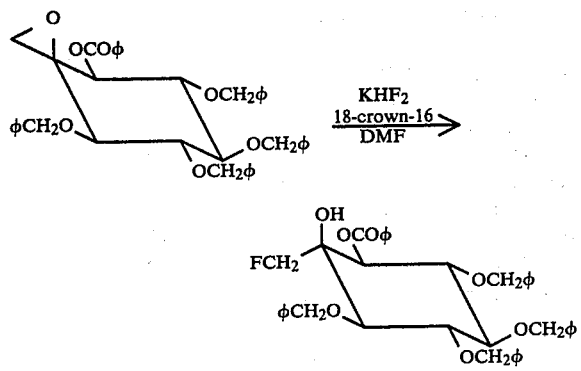

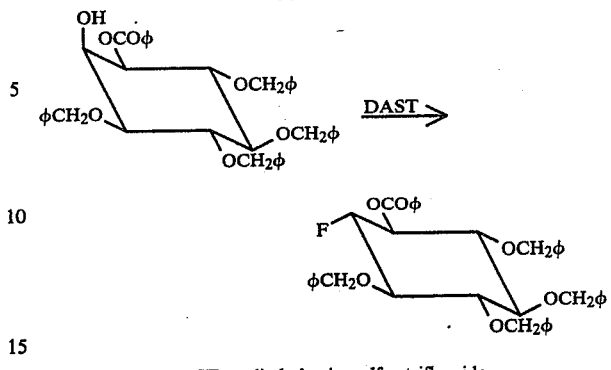

DAST = diethylaminosulfur trifluoride

This invention also relates to a method of treating inflammation in patients using a compound of Formula (I) as the active constituent. The anti-inflammatory activity of these compounds is shown below in Table I by their effectiveness in the inhibition of human platelet enzymes.

TABLE I

A. Protocol - Phosphatidyl inositol-specific phospholipase C assays. The assays were performed as follows: A mixture of PI (Sigma) and ($^3$H—inositol)-PI in CHCl$_3$ are blown to dryness under N$_2$ and sonicated into a buffer containing DOC and CaCl$_2$ so that the final concentrations in each 200 λ assay are:
250 μm PI
1 μM $^3$H—PI
0.5 mM CaCl$_2$
0.5 mg/ml DOC containing an appropriate amount of an active compound
in 50 mM Hepes, 100 mM NaCl, 0.5 mg/ml BSA pH 7.
An aliquot of sonicated human platelets,
5 × 10$^9$/ml, is added; the reaction is stopped after 10 minutes with a chloroform/methanol/H$_2$O solution and the upper water phase is counted to detect water-soluble inositol counts. The pH was checked during each assay using pH paper to verify that none of the compounds affected this parameter.
B. Results: Specific phospholipase C inhibition as shown below:

| | Conc. | % Inhibition |
|---|---|---|
| myo-inositol-6 (or 5)-dodecanecarbamate | 0.8 mM | 16 |
| myo-inositol-5 (or 6)-palmitate | 1.22 mM | 55 |
| | 0.122 mM | 7 |

Accordingly, the compounds of Formula (I) and (II) of the present invention can be used to reduce inflammation and relieve pain in diseases such as emphysema, rheumatoid arthritis, osteoarthritis, gout, bronchial inflammation, infectious arthritis, rheumatic fever and the like.

For treatment of inflammation, fever or pain, the compounds of Formula (I) and (II) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation.

Formulations for oral use include tablets which contain the active ingredient in admixture with non-toxic pharmaceutically acceptable excipients. These excipients may be, for example, inert diluents, such as calcium carbonate, sodium carbonate, lactose, calcium phosphate or sodium phosphate; granulating and disintegrating agents, for example, maize starch, or alginic acid; binding agents, for example, starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

Aqueous suspensions usually contain the active materials in admixture with appropriate excipients. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents which may be a naturally-occurring phosphatide, for example, lecithin; a condensation product of an alkylene oxide with a fatty acid, for example, polyoxyethylene stearate; a condensation product of ethylene oxide with a long chain aliphatic alcohol, for example, heptadecaethyleneoxycetanol; a condensation product of ethylene oxide with a partial ester derived from fatty acids and a hexitol such as polyoxyethylene sorbitol monooleate; or a condensation product of ethylene oxide with a partial ester derived from fatty acids and hexitol anhydrides, for example, polyoxyethylene sorbitan monooleate. The aqueous suspensions may also contain one or more preservatives, for example, ethyl, n-propyl, or p-hydroxybenzoate; one or more coloring agents; one or more flavoring agents; and one or more sweetening agents such as sucrose or saccharin.

Oily suspension may be formulated by suspending the active ingredient in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The pharmaceutical compositions of the invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally-occurring gums, for example, gum acacia or gum tragacanth; naturally-occurring phosphatides, for example, soybean lecithin; and esters including partial esters derived from fatty acids and hexitol anhydrides, for example, sorbitan mono-oleate, and condensation products of the said partial esters with ethylene oxide, for example, polyoxyethylene sorbitan monooleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may be a sterile injectable solution or suspension in a non-toxic parenterally-acceptable diluent or solvent. Among the acceptable vehicles and solvents that may be employed are water, 1,3-butanediol, Ringer's solution and isotonic sodium chloride solution. In addition, sterile fixed oils are conventionally employed as a solvent or suspending medium. For this purpose any bland fixed oil may be employed including synthetic mono- or diglycerides. Fatty acids such as oleic acid also find use in the preparation of injectables.

The compounds of Formula (I) and (II) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug, for example, cocoa butter and polyethylene glycols.

For topical use, creams, ointments, jellies, solutions, suspensions or the like containing the anti-inflammatory agents are employed according to methods recognized in the art.

Dosage levels of the order from 0.2 mg to 140 mg per kilogram of body weight per day are useful in the treatment of the above-indicated conditions (10 mg to 7 gms. per patient per day). For example, inflammation is effectively treated and anti-pyretic and analgesic activity manifested by the administration from about 0.5 to 50 mg of the compound per kilogram of body weight per day (25 mg to 3.5 gms per patient per day). Preferably, a dosage of from about 2 mg to about 20 mg per kilogram of body weight per day is use to produce effective results (50 mg to 1 gm per patient per day).

The amount of active ingredient that may be combined with the carrier materials to produce a single dosage form will vary depending upon the host treated and the particular mode of administration. For example, a formulation intended for the oral administration of humans may contain from 5 mg to 5 gm of active agent compounded with an appropriate and convenient amount of carrier material which may vary from about 5 to about 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general heath, sex, diet, time of administration, route of administration, rate of excretion, drug combination and the severity of the particular disease undergoing therapy.

EXAMPLE 1

DL-1-O-Trifluoromethanesulfonylmyoinositol

Step A: Preparation of DL-3,4,5,6-tetra-O-benzyl-1-O trifluoromethanesulfonylmyoinositol To a stirred solution of DL-1,4,5,6-tetra-O-benzyl-myoinositol (1.08 g) in dry methylene chloride (25 ml) containing dry pyridine (1.0 ml) at $-15°$ to $-20°$ under nitrogen was added a solution of trifluoromethanesulfonic anhydride (0.38 ml) in methylene chloride (3 ml) over 15 minutes. The mixture was stirred at $-15°$ for 1 hour, at 0° for 0.5 hour and then at room temperature for 0.5 hours before quenched with cold 5% sodium bicarbonate solution. The organic phase was washed with water, brine and dried ($Na_2SO_4$). Removal of solvent gave the crude product which was purified by passing through a short silica gel column with 50% ethyl acetate in hexane and subsequent recrystallization from 5% ethyl acetate in hexane to afford 1.08 g of crystalline DL-3,4,5,6-tetra-O-benzyl-1-O-trifluoromethanesulfonylmyoinositol (80% yield): m.p. 112°–113° (dec.).

Anal. Calcd. for $C_{35}H_{35}F_3O_8S$: C, 62.49; H, 5.24; F, 8.47; S, 4.77. Found: C, 62.85; H, 5.26; F, 8.60; S, 4.98.

Step B: Preparation of DL-1-O-trifluoromethanesulfonylmyoinositol

To a stirred solution of DL-3,4,5,6-tetra-O-benzyl-1-O-trifluormethanesulfonylmyoinositol (0.8 g) in glacial acetic acid (25 ml) at 10° to 15° is added 30% HBr-AcOH (10 ml) during 15 minutes. The mixture is stirred at room temperature for 5 hours and cooled to 10°. The crystals are collected, washed with ether-AcOH, ether and dried to give DL-1-O-trifluoromethanesulfonyl-myoinositol.

EXAMPLE 2

DL-2-O-Methyl-1-myoinosityl oxalate monoester

Step A: Preparation of benzyl DL-2-O-methyl-3,4,5,6-tetra-O-benzyl-1-myoinosityl oxalate To a solution of DL-2-O-methyl-3,4,5,6-tetra-O-benzylmyoinositol (5.54 g) and benzyl oxalate monoester (1.80 g) in dry pyridine (25 ml) at 110° to 120° is added dicyclohexylcarbodiimide (8.0 g). The mixture is heated at 110° to 120° until the reaction is complete, and diluted with water (1 ml) at room temperature. The solid is removed by filtration and the filtrate is concentrated in vacuo to a residue which is recrystallized from chloroform-hexane to give benzyl DL-2-O-methyl-3,4,5,6-tetra-O-benzyl-1-myoinosityl oxalate.

Step B: Preparation of DL-2-O-methyl-1-myoinosityl oxalate monoester

A solution of benzyl DL-2-O-methyl-3,4,5,6-tetra-O-benzyl-1-myoinosityl oxalate (1.5 g) in 80% ethanol (50 ml) is hydrogenolyzed with atmospheric hydrogen in the presence of palladium black (0.75 g) for 5 hours. The resulting mixture is filtered and the filtrate concentrated to give crystalline DL-2-O-methyl-1-myoinosityl oxalate monoester.

EXAMPLE 3

DL-1-Deoxy-2-myoinosityloxyacetic acid

Step A: Preparation of Benzyl DL-1-deoxy-3,4,5,6-tetra-O-benzyl-2-myoinosityloxyacetate To a refluxing solution of DL-1-deoxy-3,4,5,6-tetra-O-benzylmyoinositol (5.24 g) and potassium t-butoxide (4.48 g) in t-butanol (50 ml) is added benzyl bromoacetate (1.5 g) dropwise over 15 minutes. The mixture is heated at reflux overnight. The mixture is filtered, and the filtrate is concentrated to dryness. The residue is recrystallized from ethanol-hexane to give benzyl DL-1-deoxy-3,4,5,6-tetra-O-benzyl-2-myoinosityloxyacetate.

Step B: Preparation of DL-1-deoxy-2-myoinosityloxyacetic acid

A solution of benzyl DL-1-deoxy-3,4,5,6-tetra-O-benzyl-2-myoinosityloxyacetate (1.5 g) in 80% ethanol (50 ml) is hydrogenolyzed with atmospheric hydrogen in the presence of palladium black (0.75 g) for 4 hours. The catalyst is removed by filtration and the filtrate concentrated. The residue is recrystallized from ethanol to give DL-1-deoxy-2-myoinosityloxyacetic acid.

EXAMPLE 4

5-(and 6-)hexadecanoyl-myo-inositol

Step A: Preparation of 5- and 6-hexadecanoyl-1,2:3,4-dicyclohexylidene myo-inositol To a mixture of 0.68 g of 1,2:3,4-dicyclohexylidene inositol in 10 ml pyridine stirred at 0° was added dropwise 0.58 g of palmitoyl chloride. After stirring for 30 minutes at 0° and 17 hours at 22° the mixture was evaporated under reduced pressure and the residue of 1.64 g was chromatographed on Baker silica gel using methylene chloride and methylene chloride/ethyl acetate mixtures to afford 0.76 g of crude 5- and 6-hexadecanoyl derivatives. The two isomers were separated by HPLC using 5% ethyl acetate on a Porosil A column 2-(2'×⅜").

The earlier eluting isomer, 141.1 mg, contained a small amount of the isomer, so it was chromatographed on 2–500μ 8"×8" silica gel G plates using 10% ethyl acetate in methylene chloride. The sample, 135 mg, had m.p. 72°–74°.

Anal. Calcd. for $C_{34}H_{58}O_7$: C, 70.55; H, 10.10. Found: C, 70.85; H, 10.28.

Mass spectrum: 578 (M+); 535 (M+-43).

The later eluting isomer, 397.7 mg, had mass spectrum 578 (M+); 535 (M+-43).

Step B: Preparation of 5-(and 6-)hexadecanoyl)-myo-inositol

A sample of 30.7 mg of 5-(or 6-)hexadecanoyl-1,2:3,4-dicylohexylidene-myo-inositol in 2 ml tetrahydrofuran and 0.7 ml water was stirred at 22° in the presence of 0.3 g Nafion-H ion exchange resin for 4½ days. The reaction mixture was filtered and the residue washed with tetrahydrofuran/water. The combined aqueous tetrahydrofuran solvents were evaporated under reduced pressure to give a residue. The residue was triturated with methylene chloride and dried in vacuo to provide 20.8 mg of product. Whereas the starting material had an $R_f$ value of 0.8 (silica gel G, 10% ethyl acetate in methylene chloride), the product showed only a spot at the origin ($R_f$ NO).

The mass spectrum of the product after per-trimethylsilylation showed m/e 778 (M+) and 763 (M+-15) in the upper region of the spectrum.

In similar manner to the procedure described above the slower running isomer obtained in procedure 5 above was treated to remove the dicyclohexylidene protecting groups. From 41.5 mg of this isomer there was obtained 11.3 mg of product. This isomer had an $R_f$ O in a t.l.c. system of 25% ethyl acetate in methylene chloride. The mass spectrum of its per-trimethylsilyl derivative showed m/e 778 (M+) and 763 (M+-15).

Just as described above for the hexadecanoyl derivatives so too can other acyl derivatives of inositol be converted from their protected dicyclohexylidene derivatives to the unprotected acyl-myo-inositols.

EXAMPLE 5

5- and 6-Hexadecanesulfonyl-myo-inositol

Step A: Preparation of 5- and 6-hexadecanesulfonyl-1,2:3,4-dicyclohexylidene-myo-inositol To 0.68 g of 1,2:3,4-dicyclohexylidene-myo-inositol in 10 ml pyridine stirred at 0° was added 0.65 g of hexadecanesulfonyl chloride. The reaction mixture was allowed to warm to 22° and then stirred for 20 hours. The volatiles were removed under reduced pressure and the residue of 1.78 g was chromatographed on 25 g Baker silica gel using methylene chloride and methylene chloride/ethyl acetate to provide 0.58 g of a mixture of the two hexadecanesulfonyl derivatives.

The isomers were purified by HPLC using Porosil A and 5% ethyl acetate in methylene chloride. The earlier eluting isomer, 162.7 mg, was obtained as a crystalline solid, m.p. 123.5°–125°.

Anal. Calcd. for $C_{34}H_{60}O_8S$: C, 64.93; H, 9.62; S, 5.10. Found: C, 64.51; H, 9.60; S, 4.95.

Mass spectrum: 628 (M+); 585 (M-43).

The later eluting isomer, 285.3 mg, did not crystallize. Mass spectrum: 628 (M+); 585 (M-43). The 300 MHz NMR spectrum of this isomer was distinctly different from that of the other.

Step B: Preparation of 5- and 6-hexadecanesulfonyl-myo-ionositol

A mixture of 43.5 mg of 5-(or 6-)hexadecanesulfonyl-1,2:3,4-dicyclohexylidene (earlier eluting isomer) in 1.6 ml glacial acetic acid and 0.4 ml water was heated on a steam bath for 2 hours, during which time a precipitate appeared. The material was removed by filtration and dried to give 22.5 mg crude product. After triturating with methylene chloride and drying, the precipitate weighed 21.4 mg.

Anal. Calcd. for $C_{22}H_{44}O_8S$: C, 56.38; H, 9.46. Found: C, 54.88; H, 9.52.

The mass spectrum of the per-trimethylsilyl derivative showed high mass peaks at m/e 756 (M+) and 741 (M+-15), indicating incomplete silylation (only four of five possible hydroxyl groups were silylated).

In a similar manner, a sample of 46.6 mg of the slower eluting isomer was deblocked to give 26.8 mg of product.

Anal. Calcd. for $C_{22}H_{44}O_8S$: C, 56.38; H, 9.46; S, 6.84. Found: C, 56.32; H, 9.53; S, 6.81.

The mass spectrum of this material after per-trimethylsilylation showed high mass peaks at m/e 828 (M+) and 813 (M+-15) indicative of complete trimethylsilylation as well as peaks at m/e 756 (M+) and 741 (M+-15) for the derivative with one unsilylated hydroxyl.

The nmr spectra of both products were taken in DMSO-$d_6$. The downfield regions of each showed no signals corresponding to those of the other isomer.

In a similar manner, other alkanesulfonyl dicyclohexylidene myo-inositols may be converted to the corresponding alkanesulfonyl-myo-inositols.

EXAMPLE 6

5-(and 6-)-dodecylcarbamoyl-myo-inositol

Step A: Preparation of 5- and 6-dodecylcarbamoyl-1,2:3,4-dicyclohexylidene myo-inositol To 0.6853 g of 1,2:3,4-dicyclohexylidene myo-inositol in 10 ml of methylene chloride was added 0.4 g of dodecylisocyanate. After refluxing overnight, the solvent was removed by evaporation and the residue chromatographed on 25 g Baker silica gel using methylene chloride and methylene chloride/ethyl acetate as eluant. The material eluting with 5–25% ethyl acetate, 790.4 mg, was a mixture of the two isomeric products. This material was separated by HPLC into two discrete isomers using 8% ethyl acetate in methylene chloride with 2-2'×⅜" Porosil A columns.

The first eluted spot, 366 mg, had a mass spectrum of its trimethylsilyl derivative with m/e 623 (M+) and 608 (M+-CH$_3$). It was assigned the 5-dodecylcarbamoyl structure on the basis of its 300 MHz NMR spectrum.

The second eluted spot, 144 mg, had a mass spectrum of its trimethylsilyl derivative with m/e 623 (M+) and 608 (M+-CH$_3$). It was assigned the 6-dodecylcarbamoyl structure on the basis of its 300 MHz NMR spectrum, which was distinctly different from that of the C-5 isomer.

Other material obtained from early fractions of the column and high pressure liquid chromatography was combined. Its mass spectrum showed weak 762 m/e (M+) with weak 719 (M+-43), indicating its structure to be the 5,6-di(dodecylcarbamoyl)-derivative.

Step B: Preparation of 5- and 6-dodecylcarbamoyl-myo-inositol

A sample of 125.4 mg of the front running 5-dodecylcarbamoyl-1,2:3,4-dicyclohexylidene-myo-inositol was heated for 2 hours on a steam bath in 8 ml glacial acetic acid and 2 ml water. After cooling water was added to transfer the flask contents and precipitation occurred, the product precipitate after filtering, drying and trituration with methylen chloride weighed 69.3 mg.

Anal. Calcd. for $C_{19}H_{37}NO_7$: C, 58.29; H, 9.53; N, 3.58. Found: C, 58.33; H, 9.68; N, 3.38.

The mass spectrum of the per-trimethylsilyl derivative showed peaks at m/e 751 (M+) and 736 (M+-15) and a large 664 (M+-15) for tetra-silyl derivative).

From 91.5 mg of the slower running 6-dodecylcarbamoyl-1,2:3,4-dicyclohexylidene-myo-inositol using 4.8 ml of glacial acetic acid and 1.2 ml water heated on a steam bath for 2 hours there was obtained 47.0 mg of product, the other isomer of 6-dodecylcarbamoyl-myo-inositol.

Anal. Calcd. for $C_{19}H_{37}NO_7$: C, 58.29; H, 9.53; N, 3.58. Found: C, 57.97; H, 9.61; N, 3.51.

The mass spectrum of the per-trimethylsilyl derivative showed peaks at m/e 751 ($M^+$) and 736 ($M^+$-15).

In similar manner other alkylcarbamoyl dicyclohexylidene myo-inositol derivatives may be converted to the corresponding alkylcarbamoyl-myo-inositols.

What is claimed is:

1. A compound of formula:

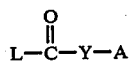
(II)

wherein:
L is $R^1NH$ wherein $R^1$ is
  (1) straight or branched-chain alkyl having from 1 to 20 carbon atoms;
  (2) aryl having from 6 to 10 carbon atoms with the proviso that L cannot be p-tolyl when A is myo-inositol;
  (3) cycloalkyl having from 3 to 8 carbon atoms;
  (4) alkenyl having from 2 to 20 carbon atoms;
  (5) cycloalkenyl having from 5 to 8 carbon atoms;
Y is oxygen or —NH—; and
A is

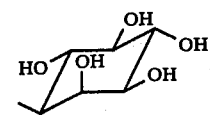
(a)

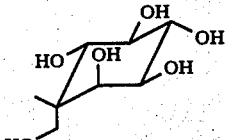
(b)

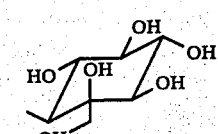
(c)

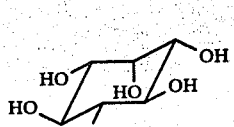
(d)

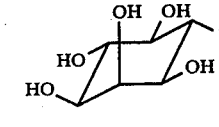
(e)

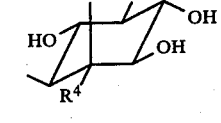
(f)

wherein $R^4$ is methyl, fluoromethyl, trifluoromethyl or 2-methoxyethyl or

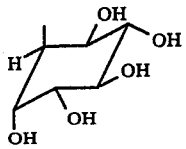
(g)

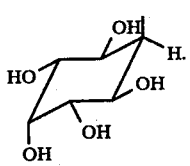
(h)

2. The compound of claim 1 wherein:
L is $R^1NH$;
Y is oxygen or —NH—; and
A is

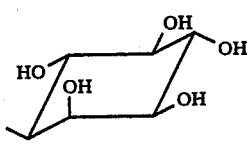
(a)

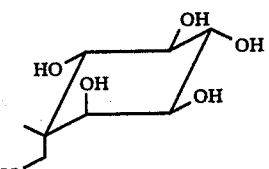
(b)

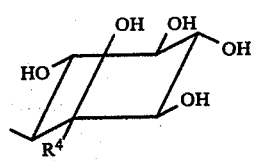
(c)

wherein $R^4$ is methyl, fluoromethyl, trifluormethyl or 2-methoxyethyl

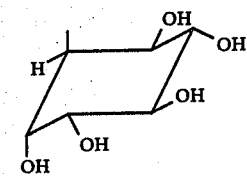
(d)

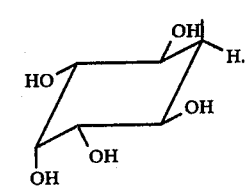
(e)

3. The compound of claim 1 which is 5-dodecylcarbamoylmyo-inositol.

4. A pharmaceutical composition for treating inflammatory conditions, fever and pain in mammalian species comprising a non-toxic pharmaceutical carrier and an effective amount of a compound of formula:

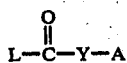

wherein:
L is R¹NH wherein R¹ is
  (1) straight or branched-chain alkyl having from 1 to 20 carbon atoms;
  (2) aryl having from 6 to 10 carbon atoms with the proviso that L cannot be p-tolyl when A is myo-inositol;
  (3) cycloalkyl having from 3 to 8 carbon atoms;
  (4) alkenyl having from 2 to 20 carbon atoms;
  (5) cycloalkenyl having from 5 to 8 carbon atoms;
Y is oxygen or —NH—; and
A is

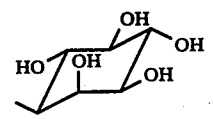 (a)

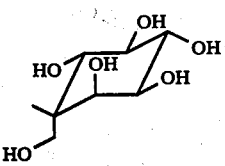 (b)

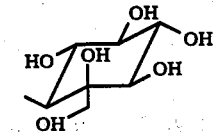 (c)

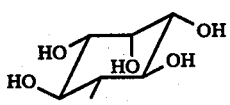 (d)

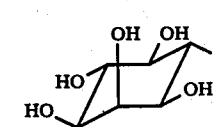 (e)

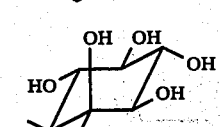 (f)

wherein R⁴ is methyl, fluoromethyl, trifluoromethyl or 2-methoxyethyl or

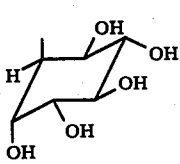 (g)

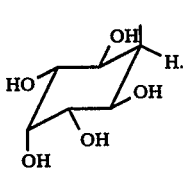 (h)

5. The compound of claim 4 wherein:
L is R¹NH;
Y is oxygen or —NH—; and
A is

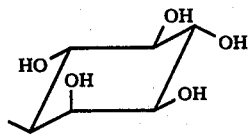 (a)

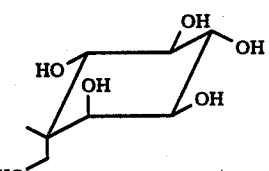 (b)

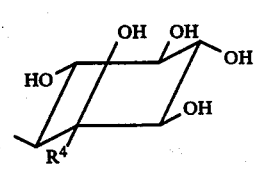 (c)

wherein R⁴ is methyl, fluoromethyl, trifluormethyl or 2-methoxyethyl

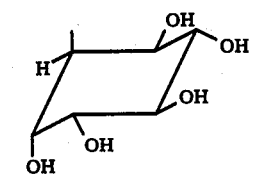 (d)

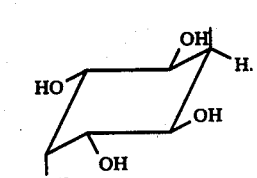 (e)

6. A method for treating inflammatory conditions, fever and pain comprising the administration to a mammalian species in need of such treatment an effective amount of a compound of structural formula:

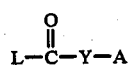

wherein:
L is R¹NH wherein R¹ is
  (1) straight or branched-chain alkyl having from 1 to 20 carbon atoms;
  (2) aryl having from 6 to 10 carbon atoms with the proviso that L cannot be p-tolyl when A is myo-inositol;
  (3) cycloalkyl having from 3 to 8 carbon atoms;
  (4) alkenyl having from 2 to 20 carbon atoms;
  (5) cycloalkenyl having from 5 to 8 carbon atoms;
Y is oxygen or —NH—; and
A is

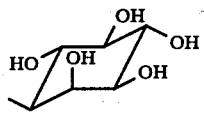 (a)
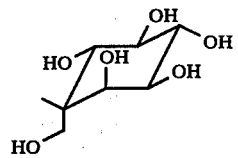 (b)
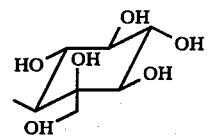 (c)
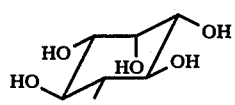 (d)
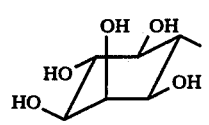 (e)
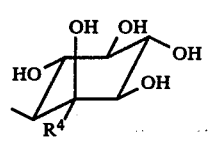 (f)
wherein R⁴ is methyl, fluoromethyl, trifluoromethyl or 2-methoxyethyl or
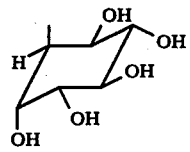 (g)
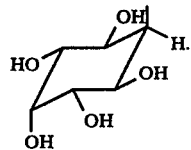 (h)
7. The compound of claim 6 wherein:
L is R¹NH;
Y is oxygen or —NH—; and
A is
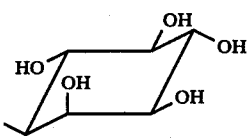 (a)
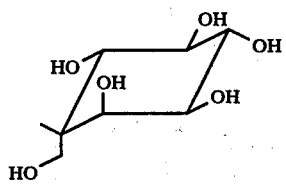 (b)
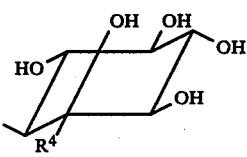 (c)
wherein R⁴ is methyl, fluoromethyl, trifluormethyl or 2-methoxyethyl
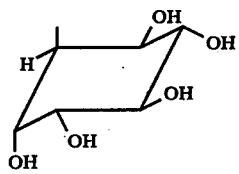 (d)
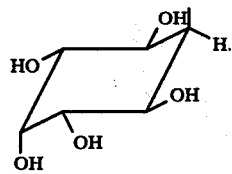 (e)
* * * * *